United States Patent
Shpunt

(10) Patent No.: US 9,523,625 B2
(45) Date of Patent: Dec. 20, 2016

(54) DETECTING FAILURE OF SCANNING MIRROR

(71) Applicant: PRIMESENSE LTD., Tel Aviv (IL)

(72) Inventor: Alexander Shpunt, Tel Aviv (IL)

(73) Assignee: APPLE INC., Cupertino, CA (US)

( * ) Notice: Subject to any disclaimer, the term of this patent is extended or adjusted under 35 U.S.C. 154(b) by 0 days.

(21) Appl. No.: 14/433,688

(22) PCT Filed: Dec. 12, 2013

(86) PCT No.: PCT/IB2013/060839
§ 371 (c)(1),
(2) Date: Apr. 6, 2015

(87) PCT Pub. No.: WO2014/091435
PCT Pub. Date: Jun. 19, 2014

(65) Prior Publication Data
US 2015/0276547 A1  Oct. 1, 2015

Related U.S. Application Data

(60) Provisional application No. 61/736,551, filed on Dec. 13, 2012.

(51) Int. Cl.
*G01B 9/00* (2006.01)
*G01M 11/00* (2006.01)
(Continued)

(52) U.S. Cl.
CPC ............ *G01M 11/005* (2013.01); *B81B 3/004* (2013.01); *B81C 1/00015* (2013.01);
(Continued)

(58) Field of Classification Search
CPC ........ G01M 11/00; G01N 27/00; F16D 11/06; H01L 21/66; G06F 19/00; G03B 21/28; G01R 33/02
See application file for complete search history.

(56) References Cited

U.S. PATENT DOCUMENTS 4,630,355 A * 12/1986 Johnson .............. H01L 23/5382
148/DIG. 55
6,847,907 B1 * 1/2005 Novotny ............. B81C 99/0045
438/17
(Continued)

FOREIGN PATENT DOCUMENTS

EP        1538475 A1    6/2005
JP    2004334966 A    11/2004
(Continued)

OTHER PUBLICATIONS

International Application # PCT/IB2013/060839 Search Report dated Apr. 24, 2014.
(Continued)

*Primary Examiner* — Tarifur Chowdhury
*Assistant Examiner* — Jamil Ahmed
(74) *Attorney, Agent, or Firm* — D. Kligler IP Services Ltd.

(57) ABSTRACT

A method for monitoring includes providing a device (64) including a first part (46) and a second part (72) and a movable joint (70) connecting the first part to the second part. An electrical characteristic of a conductive path (80) crossing the movable joint is measured, and a remedial action is initiated in response to detecting a change of the electrical characteristic.

16 Claims, 2 Drawing Sheets

(51) Int. Cl.

| | | |
|---|---|---|
| *B81C 99/00* | (2010.01) | |
| *G02B 26/08* | (2006.01) | |
| *B81B 3/00* | (2006.01) | |
| *B81C 1/00* | (2006.01) | |
| *G01N 27/00* | (2006.01) | |
| *G01R 31/02* | (2006.01) | |
| *H01L 21/306* | (2006.01) | |

(52) U.S. Cl.
CPC .......... *B81C 99/003* (2013.01); *G01N 27/00* (2013.01); *G01R 31/026* (2013.01); *G02B 26/0833* (2013.01); *H01L 21/306* (2013.01); *B81B 2201/042* (2013.01); *B81B 2203/058* (2013.01)

(56) References Cited

U.S. PATENT DOCUMENTS

| | | | |
|---|---|---|---|
| 7,952,781 B2 | 5/2011 | Weiss et al. | |
| 2003/0020472 A1* | 1/2003 | Kretschmann | G01R 33/0286 |
| | | | 324/259 |
| 2004/0070806 A1 | 4/2004 | Ryu et al. | |
| 2005/0007562 A1* | 1/2005 | Seki | G03B 21/2086 |
| | | | 353/98 |
| 2005/0122602 A1* | 6/2005 | Kamiya | G02B 26/085 |
| | | | 359/849 |
| 2006/0125597 A1 | 6/2006 | Kamiya et al. | |
| 2007/0089973 A1 | 4/2007 | Inui et al. | |
| 2013/0207970 A1 | 8/2013 | Shpunt et al. | |
| 2013/0229188 A1 | 9/2013 | Seymour et al. | |
| 2013/0250387 A1 | 9/2013 | Chayat | |

FOREIGN PATENT DOCUMENTS

| | | |
|---|---|---|
| JP | 2008203497 A | 9/2008 |
| WO | 0218979 A2 | 3/2002 |
| WO | 2014016794 A1 | 1/2014 |
| WO | 2014064606 A1 | 5/2014 |

OTHER PUBLICATIONS

Awtar et al., "Two-Axis Optical Mems Scanner", Proceedings of the ASPE 2005 Annual Meeting, Paper No. 1800, 4 pages, 2005.

* cited by examiner

DETECTING FAILURE OF SCANNING MIRROR

CROSS-REFERENCE TO RELATED APPLICATIONS

This application claims the benefit of U.S. Provisional Patent Application 61/736,551, filed Dec. 13, 2012, which is incorporated herein by reference.

FIELD OF THE INVENTION

The present invention relates generally to operational testing and verification of mechanical devices, and particularly to techniques for verifying the integrity of micro-electro-mechanical systems (MEMS) devices.

BACKGROUND

MEMS devices are found in a wide range of applications, as diverse as optical scanners, automotive pressure sensors and accelerometers, and gyroscopes used in computing and communication devices. MEMS-based optical scanners are described, for instance, in U.S. Pat. No. 7,952,781 and in U.S. Patent Application Publication 2013/0207970, whose disclosures are incorporated herein by reference.

Methods for monitoring the operation of a scanning mirror are known in the art. For example, U.S. Patent Application Publication 2013/0250387, whose disclosure is incorporated herein by reference, describes a transmitter, which is configured to emit a beam comprising pulses of light, and a scanning mirror, which is configured to scan the beam over a scene. A receiver is configured to receive the light reflected from the scene and to generate an output indicative of the pulses returned from the scene. A grating is formed on an optical surface in the apparatus and is configured to diffract a portion of the beam at a predetermined angle, so as to cause the diffracted portion of the beam to be returned from the scanning mirror to the receiver. A controller is coupled to process the output of the receiver so as to detect the diffracted portion and to monitor a scan of the mirror responsively thereto.

SUMMARY

Embodiments of the present invention that are described herein provide methods and apparatus that can be used to test and verify the integrity of hinged mechanical devices.

There is therefore provided, in accordance with an embodiment of the present invention, a method for monitoring, which includes providing a device including a first part and a second part and a movable joint connecting the first part to the second part. An electrical characteristic of a conductive path crossing the movable joint is measured. A remedial action is initiated in response to detecting a change of the electrical characteristic.

In some embodiments, providing the device includes applying photolithographic processing to etch the first and second parts of the device and the joint from a substrate and to deposit a metal trace so as to form the conductive path on a surface of the substrate. In a disclosed embodiment, the device includes a micro-electro-mechanical system (MEMS), and the substrate includes a semiconductor wafer.

Typically, measuring the electrical characteristic includes measuring an electrical continuity of the conductive path, and detecting the change includes detecting a loss of the continuity in response to a failure of the joint.

In one embodiment, the first part of the device includes a mirror and the second part of the device includes a gimbal, and the movable joint includes rotatable hinges between the mirror and the gimbal, and the rotatable hinges are crossed by the conductive path. The mirror may includes a conductive material, which forms a part of the conductive path. Additionally or alternatively the rotatable hinges between the mirror and the gimbal may include first hinges, and the device may include a base and second rotatable hinges between the gimbal and the base, wherein the conductive path crosses both the first and the second hinges. In a disclosed embodiment, providing the device includes directing a beam of light toward the mirror so as to scan the beam reflected from the mirror as the mirror rotates on the hinges, and initiating the remedial action includes interrupting the beam of the light.

Alternatively or additionally, initiating the remedial action includes issuing an indication of a failure of the device.

There is also provided, in accordance with an embodiment of the present invention, a mechanical device, including first and second parts and a movable joint connecting the first part to the second part. An electrical path crosses the movable joint. A control circuit is configured to measure an electrical characteristic of the conductive path and to initiate a remedial action in response to detecting a change of the electrical characteristic.

The present invention will be more fully understood from the following detailed description of the embodiments thereof, taken together with the drawings in which:

DETAILED DESCRIPTION OF EMBODIMENTS

Figure 1:
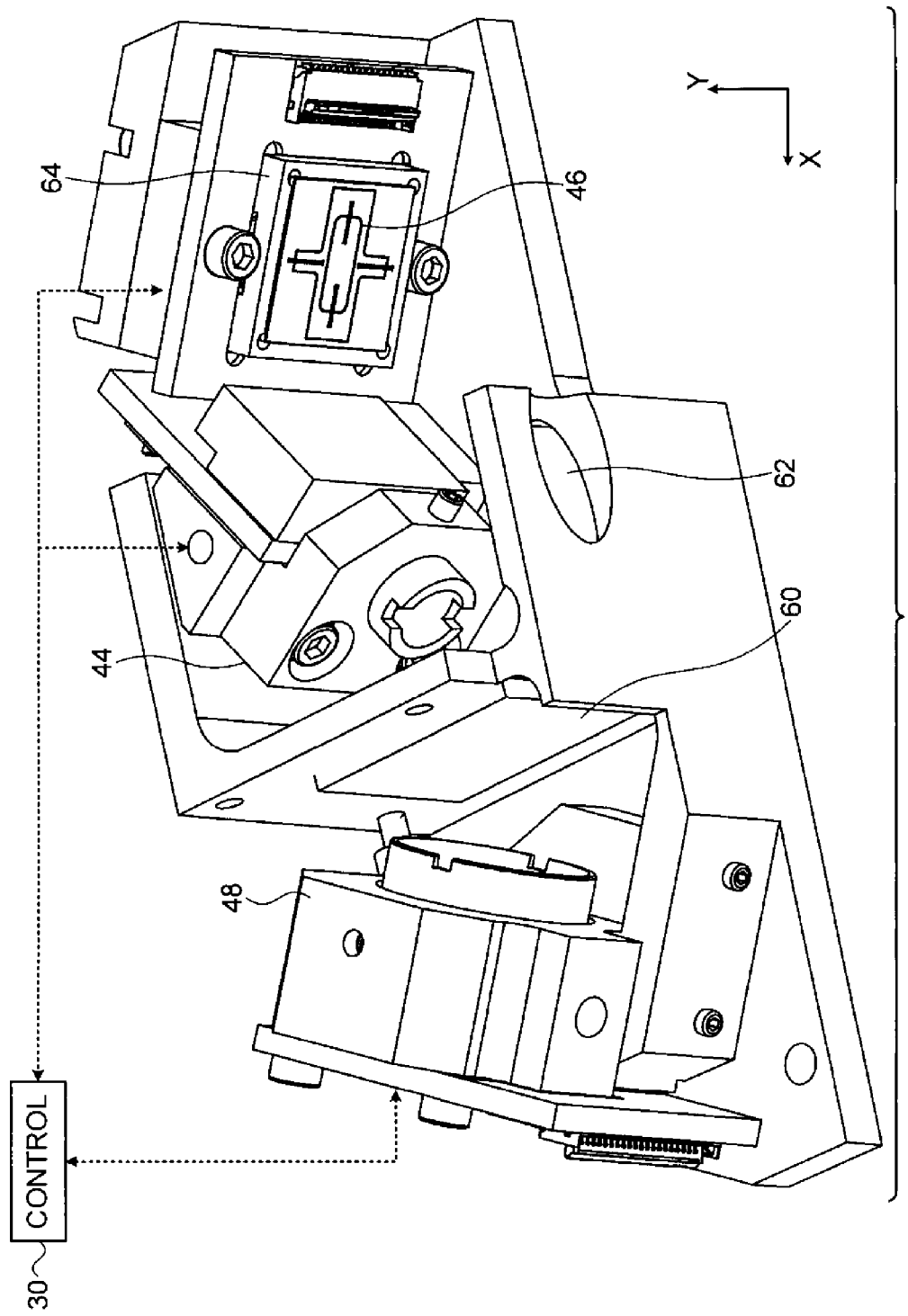
FIG. 1 is a schematic, pictorial illustration of an optical scanning head, in accordance with an embodiment of the present invention.

In some cases, structural failure of a MEMS device has to be detected with minimal delay. This sort of rapid failure detection is needed, for example, in MEMS-based scanning projector systems, in which a beam of light is emitted by a laser source and is reflected by a scanning mirror onto an object or scene, which may contain one or more people. (Systems of this sort are described in the above-mentioned U.S. Patent Application Publication 2013/0207970, as well as in PCT Patent Application PCT/IB2013/056101, filed Jul. 25, 2013, whose disclosure is incorporated herein by reference.) In such a system, if the mirror integrity is compromised and the laser beam no longer scans as intended, the light source should be shut down immediately, possibly within several microseconds or less, in order to avoid exceeding exposure limits dictated by eye safety standards.

As another example, if an accelerometer loses structural stability, it may fail to detect movement. In applications requiring immediate detection of motion, such as safety applications, it is important to detect device malfunction and take prompt action.

Embodiments of the present invention that are described herein provide devices and methods that enable real-time monitoring of the structural integrity of mechanical devices, and initiate immediate remedial action when the structural integrity is compromised. This sort of monitoring is particularly useful in detecting failure of a scanning mirror, as illustrated in the embodiment described below, but it can also be used advantageously with other types of MEMS devices, as well as in small-scale mechanical devices of other sorts. The disclosed embodiments link structural integrity with a simple electrical characteristic, such as electrical continuity (measured, for example, in terms of conductivity) of a certain path crossing the device. The device is configured and the monitored electrical characteristic is chosen so as to exhibit a sharp transition—such as loss of electrical continuity—when the device fails. The transition is easily measured with low latency, using a simple monitoring circuit.

Generally stated, embodiments of the present invention are directed to devices comprising at least first and second mechanical parts, connected by a movable joint (or multiple joints). A control circuit measures an electrical characteristic of a conductive path crossing the movable joint and initiates a remedial action in response to detecting a change of the electrical characteristic. In devices in which the first and second parts of the device and the joint are etched from a substrate by a photolithographic process (such as etching of MEMS devices from a semiconductor wafer), a metal trace may be deposited on the surface of the substrate as a part of the processing steps so as to form the conductive path on a surface of the substrate.

In a particular embodiment that is described below, the movable joints comprise rotatable hinges between a scanning mirror and a gimbal, and the conductive path crosses the rotatable hinges. Since the mirror itself typically comprises a conductive coating on the substrate, this coating may be a part of the conductive path. If a hinge breaks in operation, the control circuit will detect the loss of electrical continuity and may then interrupt the beam of light scanned by the mirror and/or issue an indication of a failure of the device.

The approach adopted by the disclosed embodiments is thus advantageous, inter alia, in that it requires only minimal additional circuitry to be added to an existing MEMS design. The conductive path itself may be deposited in the same process steps as are used to form other metal structures (such as the reflective mirror surface) in the MEMS device. Failure detection using the disclosed techniques is fast and reliable, since structural integrity can be measured directly by a circuit built into the MEMS device; and the measurement does not depend on any control loop of the scanning system, which may typically be much slower. Embodiments of the present invention thus enhance the safety and robustness of optical scanning engines, particularly for applications such as optical projection and 3D mapping, and may also be applied to other types of small-scale mechanical devices.

FIG. 1 is a schematic, pictorial illustration of an optical scanning head 40 with a scanning integrity monitor, in accordance with an embodiment of the present invention. With the exception of this monitor itself, optical scanning head 40 is similar to an optical scanning head that is described in the above-mentioned U.S. Patent Application Publication 2013/0207970. Head 40 is described here, for the sake of completeness, as an example of a device in which an embodiment of the present invention may be implemented, but without in any way limiting the application of the present invention to this specific sort of device.

Figure 2:
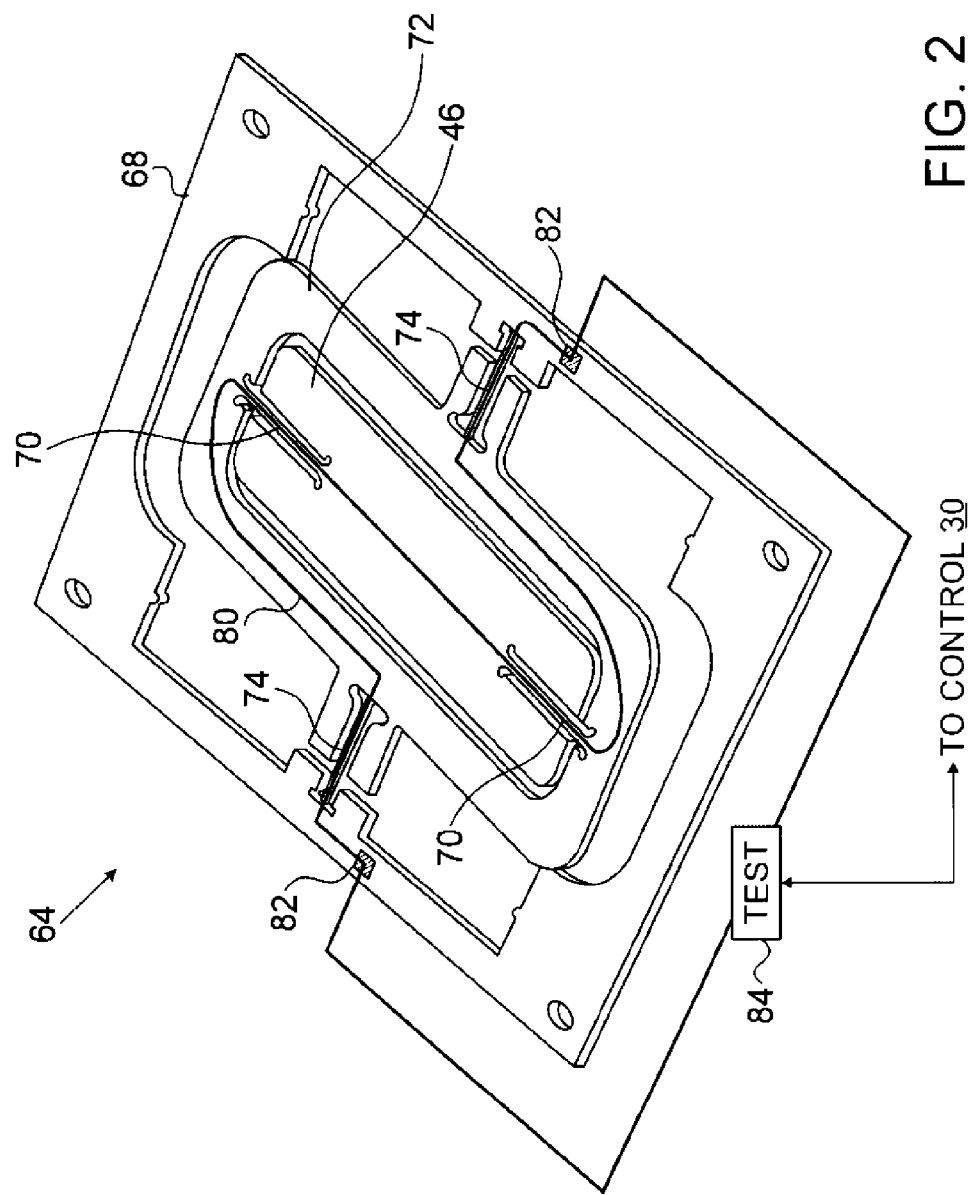
FIG. 2 is a schematic, pictorial illustration of a scanning mirror with a test circuit, in accordance with an embodiment of the present invention.

A transmitter 44, typically comprising a laser diode, emits pulses of light toward a polarizing beamsplitter 60. The light from transmitter 44 reflects off beamsplitter 60 and then a folding mirror 62 toward a scanning micromirror 46. A MEMS scanner 64 scans the micromirror in X- and Y-directions with the desired scan frequency and amplitude, causing the beam of light to scan over a scene. (The term "micromirror" is used in the present context simply to denote a small mirror, typically no more than about 10 mm across, and possibly smaller. Details of the present micromirror and scanner are shown in FIG. 2.) Light pulses reflected back from the scene strike micromirror 46, which reflects the light via folding mirror 62 through beamsplitter 60. A receiver 48 senses the returned light pulses and generates corresponding electrical pulses.

A controller 30 drives transmitter 44 and scanner 64 and analyzes the time delay between the transmitted pulses and the corresponding pulses from receiver 48 in order to measure the time of flight of each pulse. Based on this time of flight, the controller computes the depth coordinate (Z) of each point (X,Y) in the scene that is scanned by scanning head 40 and thus generates a depth map of the scene. Alternatively or additionally, the reflected light may be measured and processed in order to extract other scene characteristics. Further alternatively or additionally, controller 30 may drive transmitter and scanner in order to project an image onto the scene.

In any case, controller 30 also monitors the mechanical operation of scanner 64, as described hereinbelow. Upon receiving an indication of a malfunction, controller 30 will typically take remedial action, such as interrupting the beam from transmitter 44 (possibly by simply turning off power to the transmitter) and/or issuing an alert.

The specific mechanical and optical designs of the optical head shown in FIG. 1 are described here solely by way of example. Alternative device designs that incorporate monitoring schemes of the sort described herein are also considered to be within the scope of the present invention.

FIG. 2 is a schematic, pictorial illustration of mirror 46 and elements of MEMS scanner 64, in accordance with an embodiment of the present invention. This scanner is produced and operates on principles similar to those described in the above-mentioned U.S. Pat. No. 7,952,781, but enables two-dimensional scanning of a single micromirror, as in the above-mentioned U.S. Patent Application Publication 2013/0207970 and PCT Patent Application PCT/IB2013/056101. Alternative methods that may be used in production of scanner 64 are described in PCT Patent Application PCT/IB2013/059531, filed Oct. 22, 2013, whose disclosure is incorporated herein by reference. Alternatively, the principles of the present invention may be applied to other sorts of scanning mirrors, such as the one described by Awtar, et al., in "Two-axis Optical MEMS Scanner," Proceedings of the ASPE 2005 Annual Meeting (Norfolk, Va., Paper No. 1800, 2005). Further alternatively, the methods of integrity monitoring that are described hereinbelow may be used with mirrors that scan only in a single direction.

Micromirror 46 is produced by applying a suitable photolithographic process to a semiconductor substrate 68 and then etching the substrate to separate the micromirror from a gimbal 72, and to separate the gimbal from the remaining substrate 68. After etching, micromirror 46 (to which a suitable reflective coating is applied) is able to rotate about one axis relative to gimbal 72 on hinges 70, while gimbal 72 rotates in an orthogonal direction relative to substrate 68 on hinges 74. Scanner 64 may be driven by an electromagnetic scan drive, such as the type of drive that is described in the above-mentioned PCT Patent Application PCT/IB2013/056101.

In a typical MEMS implementation, hinges 70 and 74 are no more than 150 µm wide. The hinges may break or tear during operation due to manufacturing defects, drive circuit malfunction, physical abuse (drops, crashes), or material fatigue. These sorts of failures of one or more of the hinges will compromise or halt entirely the scan of micromirror 46, with the result that the beam reflected from the micromirror may remain fixed at the angle at which the scan ceased. The method of failure detection described herein is applicable regardless of the type of and reason for the failure.

To detect failure of any of hinges 70 and 74, a conductive trace 80 is formed across micromirror 46, gimbal 72, and substrate 68, crossing all of hinges 70 and 74 as shown. (Alternatively, if desired, the trace may be formed only across certain hinges, such as hinges 74.) Trace 80 may be deposited on substrate 68 (including all the parts etched from the substrate) using methods of printed circuit and/or microelectronics production that are known in the art. For example, when metal is deposited to form a reflective coating on the surface of micromirror 46, the trace can be part of the same metal mask as the micromirror and can be made at the same time as the as the micromirror, using the same semiconductor process steps (such as photoresist patterning, shadow mask, sputtering or electroplating). Although trace 80 is shown in FIG. 2, for the sake of clarity, as running across micromirror 46, the metal coating on the micromirror may itself serve as a part of the conductive path of the trace.

Since silicon itself is not an insulator, it will conduct some current around trace 80. Therefore it may be beneficial to introduce an insulating layer, such as silicon dioxide or silicon nitride (possibly selectively patterned), between the silicon wafer and the trace. This insulating layer may be produced using manufacturing techniques that are known in the art, such as LPCVD/PECVD or thermal growth with subsequent patterning.

Alternatively, the trace may be created by patterned doping of the silicon wafer itself, as is known in the art, or using other techniques that create a conductive path embedded in or connected to the silicon structure.

To monitor the structural integrity of scanner 64, a test circuit 84 measures the electrical continuity between test pads 82. Test circuit 84 may be mounted on substrate 68, or it may be in a separate, off-board unit. Typically, test circuit 84 measures the conductivity (or equivalently, the resistance) between pads 82. Should any of hinges 70 or 74 break or tear, the continuity of trace 80 crossing that hinge will be interrupted, breaking the electrical connection between test pads 82 and resulting in an immediate, marked decrease in conductivity (or increase of resistance). Alternatively, the test circuit may measure other electrical characteristics that may be indicative of changes in the continuity of the conductive trace.

Controller 30 receives signals from test circuit 84 that are indicative of the measured trace continuity. Alternatively, the functionality of test circuit 84 may be integrated into controller 30 itself (and for generality, the controller and test circuit are collectively referred to herein as a "control circuit"). Upon detecting a discontinuity, controller 30 initiates the appropriate remedial action, such as shutting off transmitter 44 and/or raising a malfunction alarm.

Although a conductive path with a particular topology is shown in FIG. 2, in alternative embodiments other trace patterns may be used, depending on the MEMS design and monitoring needs. The trace may be formed not only by deposition on the semiconductor substrate (on either the front or the back side), but alternatively as a conductive layer created by any other suitable electronics production technique that is known in the art. The advantages of the monitoring approach described above are thus not limited to the specific device architecture that is shown in FIG. 1, and may be realized in other sorts of MEMS devices, as well as miniature mechanical devices of other types.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for monitoring, comprising:
providing a device comprising a mirror and a gimbal and rotatable hinges between the mirror and the gimbal and having on a surface of the mirror a reflective metal coating configured to reflect and scan a beam of light that is incident on the mirror;
measuring an electrical characteristic of a conductive path crossing the rotatable hinges and including the reflective metal coating on the surface of the mirror, wherein the metal coating serves as a part of the conductive path; and
initiating a remedial action in response to detecting a change of the electrical characteristic.

2. The method according to claim 1, wherein providing the device comprises applying photolithographic processing to etch the mirror, the gimbal and the rotatable hinges from a substrate and to deposit a metal trace so as to form the conductive path, including the reflective metal coating on the surface of the mirror, on the substrate.

3. The method according to claim 2, wherein the device comprises a micro-electro-mechanical system (MEMS), and wherein the substrate comprises a semiconductor wafer.

4. The method according to claim 1, wherein measuring the electrical characteristic comprises measuring an electrical continuity of the conductive path, and wherein detecting the change comprises detecting a loss of the continuity in response to a failure of the rotatable hinges.

5. The method according to claim 1, wherein the rotatable hinges between the mirror and the gimbal comprise first hinges, and wherein the device comprises a base and second rotatable hinges between the gimbal and the base, and wherein the conductive path crosses both the first and the second hinges.

6. The method according to claim 1, wherein providing the device comprises directing the beam of light toward the mirror so as to scan the beam of light reflected from the mirror as the mirror rotates on the rotatable hinges, and wherein initiating the remedial action comprises interrupting the beam of the light.

7. The method according to claim 1, wherein initiating the remedial action comprises issuing an indication of a failure of the device.

8. A mechanical device, comprising:
a mirror and a gimbal and rotatable hinges between the mirror and the gimbal;
a conductive path crossing the rotatable hinges and including in the conductive path a reflective metal coating formed on a surface of the mirror and configured to reflect and scan a beam of light that is incident on the mirror, wherein the metal coating serves as a part of the conductive path; and a control circuit, configured to measure an electrical characteristic of the conductive path and to initiate a remedial action in response to detecting a change of the electrical characteristic.

9. The device according to claim 8, wherein the mirror, the gimbal and the rotatable hinges are etched from a substrate, and wherein the conductive path comprises a metal trace, including the reflective metal coating on the surface of the mirror, that is deposited on the substrate.

10. The device according to claim 9, wherein the mirror, the gimbal and the rotatable hinges constitute a micro-electro-mechanical system (MEMS), and wherein the substrate comprises a semiconductor wafer.

11. The device according to claim 8, wherein the electrical characteristic measured by the control circuit comprises an electrical continuity of the conductive path, and wherein the detected change comprises a loss of the continuity in response to a failure of the rotatable hinges.

12. The device according to claim 8, wherein the rotatable hinges between the mirror and the gimbal comprise first hinges, and wherein the device comprises a base and second rotatable hinges between the gimbal and the base, and wherein the conductive path crosses both the first and the second hinges.

13. The device according to claim 8, and comprising a light transmitter, which is configured to direct the beam of light toward the mirror so as to scan the beam of light reflected from the mirror as the mirror rotates on the rotatable hinges, and wherein the remedial action comprises interrupting the beam of the light.

14. The device according to claim 8, wherein the remedial action comprises issuing an indication of a failure of the device.

15. The method according to claim 3, and comprising forming an insulating layer between the substrate and the metal trace.

16. The device according to claim 10, and comprising an insulating layer between the substrate and the metal trace.

* * * * *